United States Patent [19]

Yager

[11] Patent Number: 5,206,368

[45] Date of Patent: Apr. 27, 1993

[54] PROCESS FOR EXTRACTING PYRIDINE- AND QUINOLINEDICARBOXYLIC ACIDS FROM AQUEOUS MEDIA

[75] Inventor: Richard L. Yager, Palmyra, Mo.

[73] Assignee: American Cyanamid Company, Stamford, Conn.

[21] Appl. No.: 829,397

[22] Filed: Feb. 7, 1992

Related U.S. Application Data

[63] Continuation-in-part of Ser. No. 667,832, Mar. 12, 1991, abandoned.

[51] Int. Cl.⁵ ............................. C07D 213/80
[52] U.S. Cl. ..................... 546/168; 546/321; 546/322
[58] Field of Search .............. 546/168, 321, 322

[56] References Cited

U.S. PATENT DOCUMENTS 4,460,776 7/1984 Wepplo .................. 546/250

OTHER PUBLICATIONS

Chemical Abstracts, vol. 109, No. 3, Abstract 22968t, Jul. 18, 1988, p. 620.
Chemical Abstracts, vol. 110, No. 25, Abstract 231,630m, Jun. 19, 1989, p. 648.

Primary Examiner—C. Warren Ivy
Assistant Examiner—Zinna N. Davis
Attorney, Agent, or Firm—Peggy A. Climenson

[57] ABSTRACT

The present invention provides a process for extracting pyridine- and quinolinedicarboxylic acids from aqueous media. The pyridine- and quinolinedicarboxylic acids are useful in the preparation of herbicidal 2-(2-imidazolin-2-yl)nicotinate and quinoline-3-carboxylate compounds.

17 Claims, No Drawings

PROCESS FOR EXTRACTING PYRIDINE- AND QUINOLINEDICARBOXYLIC ACIDS FROM AQUEOUS MEDIA

BACKGROUND OF THE INVENTION

This application is a continuation-in-part of U.S. patent application Ser. No. 667,832, filed on Mar. 12, 1991, now abandoned.

Pyridine- and quinolinedicarboxylic acids are employed as starting materials in the preparation of highly effective herbicidal 2-(2-Imidazolin-2-yl)-nicotinate and quinoline-3-carboxylate compounds.

European patent application 89 101 766.7 describes the preparation of substituted pyridine-2,3-dicarboxylic acids from the sequential oxidation of substituted quinolines. The application discloses the extraction of substituted pyridine-2,3-dicarboxylic acids from acidic aqueous media with tetrahydrofuran.

Pyridine- and quinolinedicarboxylic acids are amphoteric and extremely difficult to extract from aqueous media. Further, for optimal use in the preparation of herbicidal imidazolinylnicotinate and quinolinecarboxylate compounds, the starting pyridine- and quinolinedicarboxylic acid should be relatively anhydrous, i.e. free of water.

Inherent in most aqueous extraction methods is the concurrent extraction of water resulting in the presence of varying amounts of water in the extraction solvent solution.

It is an object of the present invention to provide an effective and efficient process for extracting a pyridine- or quinoline dicarboxylic acid from aqueous media. It is a further object of this invention to provide a method for obtaining the dicarboxylic acid from an aqueous medium with a minimal amount of water present in the resulting dicarboxylic acid mixture.

SUMMARY OF THE INVENTION

The present invention provides a process for extracting a pyridine- or quinolinedicarboxylic acid from an aqueous medium by mixing the aqueous medium with a binary solvent system, separating the binary solvent system to obtain a solvent of the pyridine- or quinolinedicarboxylic acid and optionally distilling said solution.

The process of the invention is especially useful in the preparation of 2-imidazolin-2-yl-nicotinate and quinoline-3-carboxylate herbicidal agents. It facilitates the recovery, recycle, isolation and delivery of the dicarboxylic acid starting material.

DETAILED DESCRIPTION OF THE INVENTION

This invention provides an efficient and effective means of extracting highly water soluble pyridine- and quinolinedicarboxylic acids from aqueous media which comprises mixing the aqueous media with a binary solvent system consisting of a water soluble solvent and an aromatic hydrocarbon, separating the binary solvent system to obtain a solution of the pyridine- or quinolinedicarboxylic acid and optionally distilling said solution.

Advantageously, the extraction of pyridine-and quinolinedicarboxylic acids from aqueous media using the inventive process yields a dicarboxylic acid solution containing significantly reduced quantities of water. The lowered presence of water allows for milder and less time consuming distillation procedures when complete removal of water is required and, further, facilitates the recycling and integration of solvent streams in a multi-step preparative process.

The binary solvent extraction of the dicarboxylic acids from aqueous media may be performed in an integral or continuous manner. The binary solvent system of the present invention consists of a water soluble solvent and an aromatic hydrocarbon, preferably present on a weight basis of about 50–90% wt/wt water soluble solvent and about 10–50% wt/wt aromatic hydrocarbon.

Water soluble solvents suitable for use in the process of the present invention include alcohols such as isopropanol, n-propanol, n-butanol and the like, ethers such as tetrahydrofuran, dioxane, ethylene glycol dimethyl ether and the like, and ketones such as acetone, methyl ethyl ketone, methyl isobutyl ketone and the like. Among the aromatic hydrocarbons which may be used in the inventive process are those having a boiling point range of about 80°–250° C. such as benzene toluene, ethylbenzene, xylenes, halobenzenes and the like, preferably toluene.

The aqueous medium containing the dicarboxylic acid may have a pH of less than 7 and preferably a pH of about 1.3 to 2.5.

Pyridine- and quinolinedicarboxylic acids which may be separated from aqueous media by the process of the invention have the formula I structure

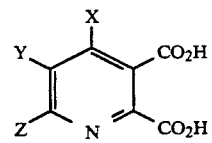

wherein
X is hydrogen or methyl; and
Y and Z are each independently hydrogen, $C_1$–$C_6$ alkyl optionally substituted with one to three $C_1$–$C_4$ alkoxy groups, $C_1$–$C_6$ alkoxy, $C_1$–$C_4$ alkylthio, phenoxy or phenyl optionally substituted with one $C_1$–$C_4$ alkyl or $C_1$–$C_4$ alkoxy group; and, when taken together, Y and Z may form a ring in which YZ is represented by the structure: —$(CH_2)_n$—, where n is an integer of 3 or 4, or

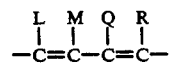

where L, M, Q and R are each hydrogen, $C_1$–$C_4$ alkyl, or $C_1$–$C_4$ alkoxy.

Particularly suitable in the process of the invention are those formula I compounds wherein
X is hydrogen; and
Y and Z are each independently hydrogen or $C_1$–$C_6$ alkyl optionally substituted with one to three $C_1$–$C_4$ alkoxy groups; and, when taken together, Y and Z may form a ring in which YZ are represented by the structure: —CH=CB=CH—.

Pyridine- and quinolinedicarboxylic acids of formula I are useful in the preparation of highly7 effective herbicidal 2-(2-imidazolin-2-yl)nicotinic or quinoline-3-carboxylic acids, esters and salts of formula II

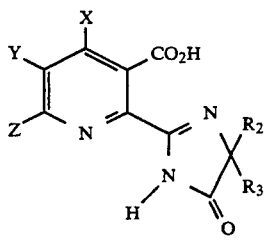

wherein

R₁ is hydrogen, an ester or a cation;
R₂ is $C_1$-$C_4$ alkyl;
R₃ is $C_1$-$C_4$ alkyl or $C_3$-$C_6$ cycloalkyl; and when R₂ and R₃ are taken together with the carbon to which they are attached they may represent $C_3$-$C_6$ cycloalkyl optionally substituted with methyl and
X, Y and Z are as described for formula I.

Among the methods of preparation for a formula II herbicidal agent which utilizes the corresponding formula I diacid are those described in U.S. Pat. Nos. 4,460,776 and 4,798,619.

In actual practice, a diester of formula III may be hydrolyzed in aqueous base to form the corresponding dicarboxylate, the aqueous solution may then be acidified to give the dicarboxylic acid of formula I which may then be separated using a binary solvent system and the thus-obtained dicarboxylic acid solution may optionally be distilled to further remove water and without further isolation, may be treated with acetic anhydride to give the intermediate of formula IV. The reaction sequence is shown in Flow Diagram I

FLOW DIAGRAM I

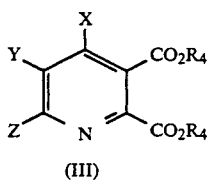

1. Base, H₂O, Δ
2. H₃O⁺
3. Binary Solvent System Extraction →

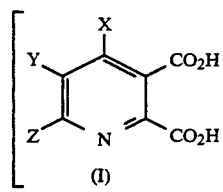

4. −H₂O
5. Acetic Anhydride

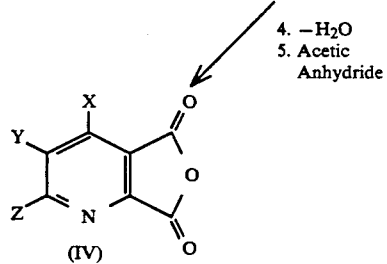

wherein R₄ is $C_1$-$C_6$ alkyl.

Aqueous media containing formula I dicarboxylic acids also may be obtained at the end of the preparation of formula II nicotinate and quinoline-carboxylate herbicides. It has now been found that unreacted formula I pyridine- and quinolinecarboxylic acids may be recovered from aqueous media in the final step in the preparation a of formula II herbicidal agent and the recovered formula I compound may be readily recycled for use in the anhydride formation shown in flow diagram I above.

Expediently, the binary solvent system containing the formula I diacid may be integrated into the existing solvent stream used in the preparative process, either as is or after distillation. The distilled binary solvent solution yields a slurry which may be filtered to give the isolated formula I diacid or may be used as is as a source of pyridine or quinolinedicarboxylic acid.

In order to facilitate a further understanding of the invention, the following examples are presented to illustrate more specific details thereof. The invention is not to be limited thereby except as defined in the claims. Unless otherwise noted, all parts are by weight. The term HPLC designates high performance liquid chromatography.

EXAMPLE 1

Recovery of 5-Ethyl-2,3-pyridinedicarboxylic acid

The pH of an aqueous medium (425.0 g) containing 0.65 wt/wt% 5-ethylene-2,3-pyridinedicarboxylic acid and 0.49 wt/wt% by-products is adjusted to pH 3.7 with sulfuric acid. Methyl isobutyl ketone (390.0 g) is added and the mixture is heated at 60° C. for 1 hour. The layers are separated and the pH of the aqueous layer is adjusted to pH 1.7 with sulfuric acid. A binary solvent system (304 g) containing 82 wt/wt% tetrahydrofuran and 18 wt/wt% toluene is added to the pH adjusted aqueous medium and the mixture is heated at 40° C. for ½ hour. The binary solvent solution is separated and distilled to near dryness. Toluene (10 g) and tetrahydrofuran (20 g) are added and distillation is continued until about 97% of the solvents are removed and 5-ethyl-2,3-pyridinedicarboxylic acid begins to crystallize. The slurry is then filtered and the filter cake is washed with toluene and dried to obtain 5-ethyl-2,3-pyridinedicarboxylic acid (2.5 g, 91% pure by HPLC analysis, 83% recovery).

EXAMPLE 2

Recovery of pyridine- and quinolinedicarboxylic acids

Following essentially the same procedure described in Example 1 and substituting the appropriate aqueous media, the following diacids are recovered:
2,3-quinolinedicarboxylic acid,
2,3-pyridinedicarboxylic acid,
5-methyl-2,3-pyridinedicarboxylic acid and
5-(methoxymethyl)-2,3-pyridinedicarboxylic acid.

EXAMPLE 3

Continuous column binary solvent extraction of 5-ethyl-2,3-pyridinedicarboxylic acid An aqueous medium (914.2 g) having a pH of 1.5 and containing 0.94 wt/wt% 5-ethyl-2,3-pyridinedicarboxylic acid is heated to 45° C. and introduced to continuous feed extraction column. A binary solvent system (464.6 g) containing 70 wt/wt% tetrahydrofuran and 30 wt/wt% toluene is simultaneously introduced to the continuous feed extraction column at a weight ratio of 0.52, binary solvent system to aqueous medium. The continuous feed extraction column has an 11.2 minute residence time (1,400 mL total volume; 71.7 mL/min aqueus medium; 42.8 mL/min binary solvent system, 45° C. column temperature). The extracted aqueous phase (910.6 g) contains 0.14 wt/wt% 5-ethyl-2,3-pyridine-dicarboxylic acid. The binary solvent extract (475.6 g) contains 1.57 wt/wt% 5-ethyl-2,3-pyridinedicarboxylic acid. After distilling the binary solvent extract (475.6 g) contains 1.57 wt/wt% 5-ethyl-2,3-pyridinedicarboxylic acid. After distilling the binary solvent extract, 5-ethyl-2,3-pyridinedicarboxylic acid (9.7 g, 77.4% pure by HPLC analysis, 87.4% recovery) is obtained.

This example demonstrates that the use of a continuous column extraction substantially reduces the ratio of the quantity of the binary solvent system to the quantity of the aqueous medium. The reduction in solvent quantity yields less energy consuming recycling requirements with a commensurately lowered environmental impact.

EXAMPLE 4

Recovery of 5-Ethyl-2,3-pyridinedicarboxylic acid using an n-butanol and toluene binary solvent system The pH of an aqueous medium (100 g) containing 0.8 wt/wt% 5-ethyl-2,3-pyridinedicarboxylic acid is adjusted to pH 1.7 with sulfuric acid. The pH adjusted aqueous medium is extracted at 40° C. with a binary solvent system (135 g) containing 74 wt/wt% n-butanol and 26 wt/wt% toluene. After distilling the binary solvent extract, 5-ethyl-2,3-pyridinedicarboxylic acid (1.4 g, 60.5% pure by HPLC analysis, 97% recovery) is obtained.

EXAMPLE 5

Comparison of a binary solvent system extraction with a single solvent extraction procedure

A. Binary Solvent System

The pH of an aqueous medium (215.0 g) containing 18.1 wt/wt% sodium 5-ethyl-2,3-pyridinedicarboxylate is adjusted to pH 1.75 with concentrated sulfuric acid (35.7 g). The pH adjusted aqueous medium is extracted with a binary solvent system (630.0 g) containing 70 wt/wt% tetrahydrofuran and 30 wt/wt% toluene. The binary solvent extract (686.3 g) obtained contains 5.4 wt/wt% (37.1 g) 5-ethyl-2,3-pyridinedicarboxylic acid and 4.4 wt/wt% (30.2 g) water as determined by HPLC analysis and Karl-Fischer titration.

B. Single solvent extraction

The pH of an aqueous medium (215.0 g) containing 18.1 wt/wt% sodium ethyl-2,3-pyridinedicarboxylate is adjusted to pH 1.75 with concentrated sulfuric acid (35.7 g). The pH adjusted aqueous medium is extracted with tetrahydrofuran (160.0 g). The tetrahydrofuran extract (232.4 g) obtained contains 16.2 wt/wt% (37.6 g) 5-ethyl-2,3-pyridinedicarboxylic acid and 18.2 wt/wt% (42.3 g) water as determined by HPLC analysis and Karl-Fischer titration.

As can be seen from the above results, significantly less water is co-extracted with the desired dicarboxylic acid when a binary solvent system is used. Further, a tetrahydrofuran/water azeotrope, which contains about 5 wt/wt% water, requires the use of additional dry solvent in order to achieve complete water removal by distillation. Advantageously, the tetrahydrofuran/toluene binary solvent system gives a toluene/water azetrope which contains about 14 wt/wt% water and essentially all of the water may be removed by distillation with no additional solvent requirements. The resultant anhydrous slurry containing the desired pyridinedicarboxylic acid and toluene may be efficiently integrated into an existing preparative process for a herbicidal 2-(4-isopropyl-4-methyl-5-oxo-2-imidazolin-2-yl)nicotinic acid.

I claim:

1. A process for extracting a pyridine- or quinolinedicarboxylic acid from an aqueous medium which comprises mixing the aqueous medium with a binary solvent system which comprises a water soluble solvent and aromatic hydrocarbon separating the binary solvent system to obtain a solution of the pyridine- or quinolinedicarboxylic acid and optionally distilling said solution.

2. The process according to claim 1 wherein the pyridine- or quinolinedicarboxylic acid is continuously extracted.

3. The process according to claim 1 wherein the water soluble solvent is present at about 50 to 90 wt/wt% and the aromatic hydrocarbon is present at about 10 to 50 wt/wt%.

4. The process according to claim 1 wherein the water soluble solvent is selected from the group consisting of tetrahydrofuran, dioxane, ethylene glycol dimethyl ether, isopropanol, n-propanol, n-butanol, acetone, methyl ethyl ketone and methyl isobutyl ketone.

5. The process according to claim 4 wherein the water soluble solvent is tetrahydrofuran.

6. The process according to claim 1 wherein the aromatic hydrocarbon is selected from the group consisting of toluene, benzene, xylene, chlorobenzene and o-dichlorobenzene.

7. The process according to claim 6 wherein the aromatic hydrocarbon is toluene.

8. The process according to claim 1 wherein the water soluble solvent is tetrahydrofuran and the aromatic hydrocarbon is toluene.

9. The process according to claim 1 wherein the aqueous medium has a pH <7.

10. The process according to claim 9 wherein the pH is about 1.3 to 2.5.

11. The process according to claim 1 wherein the pyridine- or quinolinedicarboxylic acid has the formula

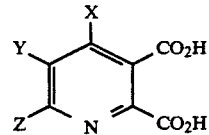

wherein
X is hydrogen or methyl; and
Y and Z are each independently hydrogen, $C_1$-$C_6$ alkyl optionally substituted with one to three $C_1$-$C_4$ alkoxy groups, $C_1$-$C_6$ alkoxy, $C_1$-$C_4$ alkylthio, phenoxy or phenyl optionally substituted with one $C_1$-$C_4$ alkyl or $C_1$-$C_4$ alkoxy group and, when taken together, Y and Z may form a ring in which YZ is represented by the structure: —$(CH_2)_n$—, where n is an integer of 3 or 4, or

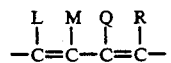

where L, M, Q and R are each hydrogen, $C_1$–$C_4$ alkyl, or $C_1$–$C_4$ alkoxy.

12. The process according to claim 11 wherein
X is hydrogen and
Y and Z are each independently hydrogen or $C_1$–$C_6$ alkyl optionally substituted with one to three $C_1$–$C_4$ alkoxy groups and, when taken together, Y and Z may form a ring in which YZ is represented by the structure:

—CH=CH—CH=CH—.

13. The process according to claim 12 wherein the pyridinedicarboxylic acid is pyridine-2,3-dicarboxylic acid.

14. The process according to claim 12 wherein the dicarboxylic acid is 5-ethyl-pyridine-2,3-dicarboxylic acid.

15. The process according to claim 12 wherein the pyridinedicarboxylic acid is 5-methyl-pyridine-2,3-dicarboxylic acid.

16. The process according to claim 12 wherein the dicarboxylic acid is 5-(methoxymethyl)-pyridine-2,3-dicarboxylic acid.

17. The process according to claim 12 wherein the dicarboxylic acid is quinoline-2,3-dicarboxylic acid.

* * * * *